(12) United States Patent
Vija et al.

(10) Patent No.: US 11,160,520 B2
(45) Date of Patent: Nov. 2, 2021

(54) MOBILE TOMOGRAPHY IMAGING

(71) Applicant: Siemens Medical Solutions USA, Inc., Malvern, PA (US)

(72) Inventors: Alexander Hans Vija, Evanston, IL (US); Michal Cachovan, Baiersdorf (DE)

(73) Assignee: Siemens Medical Solutions USA, Inc., Malvern, PA (US)

(*) Notice: Subject to any disclaimer, the term of this patent is extended or adjusted under 35 U.S.C. 154(b) by 102 days.

(21) Appl. No.: 16/801,343

(22) Filed: Feb. 26, 2020

(65) Prior Publication Data

US 2021/0259652 A1 Aug. 26, 2021

(51) Int. Cl.
*A61B 6/00* (2006.01)
*A61B 6/03* (2006.01)
*G05D 1/00* (2006.01)
*B64C 39/02* (2006.01)

(52) U.S. Cl.
CPC .............. *A61B 6/4405* (2013.01); *A61B 6/03* (2013.01); *A61B 6/4258* (2013.01); *A61B 6/461* (2013.01); *A61B 6/466* (2013.01); *A61B 6/486* (2013.01); *B64C 39/024* (2013.01); *G05D 1/0094* (2013.01); *B64C 2201/027* (2013.01); *B64C 2201/123* (2013.01); *B64C 2201/143* (2013.01)

(58) Field of Classification Search
CPC ............ B64C 39/024; B64C 2201/123; B64C 2201/143; B64C 2201/027; G05D 1/0094; A61B 6/4405; A61B 6/461; A61B 6/466; A61B 6/486; A61B 6/03; A61B 6/4258
See application file for complete search history.

(56) References Cited

U.S. PATENT DOCUMENTS

| 7,470,906 | B2 | 12/2008 | Vija | |
|---|---|---|---|---|
| 7,569,828 | B2 | 8/2009 | Vija | |
| 11,019,255 | B2* | 5/2021 | Hu | ............................ G06T 5/50 |
| 2017/0352159 | A1* | 12/2017 | Aravkin | ..................... G06T 7/50 |

FOREIGN PATENT DOCUMENTS

WO    2020032922 A1    2/2020

* cited by examiner

*Primary Examiner* — Kiho Kim

(57) ABSTRACT

A detector used for tomography imaging is mobile, allowing the detector to move about an object (e.g., patient to be imaged). A swarm of such detectors, such as a swarm of drones with detectors, may be used for tomography imaging. The trajectory or trajectories of the mobile detectors may account for the pose and/or movement of the object being imaged. The trajectory or trajectories may be based, in part, on the sampling for desired tomography. An image of an internal region of the object is reconstructed from detected signals of the mobile detectors using tomography.

20 Claims, 5 Drawing Sheets

MOBILE TOMOGRAPHY IMAGING

BACKGROUND

The present embodiments relate to tomography imaging, such as nuclear medical imaging. For tomography imaging, such as computed tomography (CT), positron emission tomography (PET), or single photon emission computed tomography (SPECT), standalone machines are usually fixed in place in a dedicated room. In SPECT, gamma camera detectors are planar detectors with about 2000 cm$^2$ area and are designed to allow the imaging of clinically relevant features without or only minimal patient truncation (e.g., a 40×50 cm$^2$ detector to axially cover at least both kidneys and image most of a patient torso). This size, including dedicating a room to one imaging system, may be costly. Patients are inconveniently brought to the imaging system, which is fixed in place. Some medical scanners have been positioned in a truck so that hospitals without a dedicated tomography imaging system may have access to such a system. The patient is brought to the truck and placed in the imaging system fixed in place in the truck. The truck-based or room-based large, single devices, do not adapt to the environment and patient being imaged.

SUMMARY

By way of introduction, the preferred embodiments described below include methods and systems for tomography imaging. A detector used for tomography is mobile, allowing the detector to move about an object (e.g., patient to be imaged). A swarm of such detectors, such as a swarm of drones with detectors, may be used for tomography imaging. The trajectory or trajectories of the mobile detectors may account for the pose and/or movement of the object being imaged. The trajectory or trajectories may be based, in part, on the sampling for desired tomography. An image of an internal region of the object is reconstructed from detected signals of the mobile detectors using tomography.

In a first aspect, a tomography medical imaging system includes a plurality of separate vehicles. Each of the separate vehicles is independently movable in two or more dimensions and has a detector. An image processor is configured to generate a two or three-dimensional representation of an internal region of a patient by tomography from signals of the detectors. A display is configured to display an image of the two or three-dimensional representation of the internal region of the patient.

In one embodiment, the plurality includes three or more of the separate vehicles. The separate vehicles may be drones moveable in three dimensions. The separate vehicles may be wheeled, tracked, or walking vehicles. In an optional swarm approach, the separate vehicles are self-organizing. The mobility may allow for the separate vehicles to travel from one room to another room to the patient.

In one embodiment, the image processor is configured to control a trajectory of each of the separate vehicles. The trajectories are based on a sampling pattern for the tomography. In a further embodiment, the image processor is configured to reconstruct by the tomography iteratively. The trajectories of the separate vehicles are controlled based, at least in part, on a previous reconstruction by the tomography.

Various detectors may be used, such as x-ray or gamma radiation detectors. In one embodiment, the detectors are solid state gamma ray detectors.

For a medical or another embodiment, the display may be an augmented reality display.

One or more of the separate vehicles or another separate vehicle may include a transmitter. The detectors on the separate vehicles are configured to detect energy responsive to a transmission from the transmitter. In other embodiments, the detectors detect emissions from the object, such as detecting emissions from radioactive decay.

In a second aspect, a method is provided for medical tomography imaging. A drone with a detector is moved about a patient. Radiation (e.g., x-ray or nuclear emission) from a patient is sensed with the detector during the moving. An image of an internal region of the patient is tomographically reconstructed from the sensed radiation. The image is displayed.

In one embodiment, the drone moves along a trajectory. The sensing includes sampling the radiation from different positions of the trajectory. The trajectory is controlled based on the sampling for the tomographically reconstructing.

The detector is one of various types. For example, a solid-state nuclear detector is used.

Other drones with other detectors, such as in a self-organizing swarm, may be moved about the patient. If the patient moves, the movement of the drone may adapt so that the drone moves based, at least in part, on movement by the patient. The drone or drones may go to the patient (e.g., the drone flies from a first location to a second location where the patient is at the second location) rather than requiring the patient to go to the tomography imaging system.

In a third aspect, a tomography imaging system includes a swarm of mobile detectors. Each of the mobile detectors is independently movable in two or more dimensions. An image processor is configured to generate, by tomography from signals from the mobile detectors, a two or three-dimensional representation of an internal region of an object. A display is configured to display an image of the object from the two or three-dimensional representation of the internal region.

In one embodiment, the object is a patient. For PET or SPECT, the mobile detectors may be drones with gamma ray detectors.

In another embodiment, the mobile detectors of the swarm are configured to follow trajectories based, at least in part, on sampling for the tomography.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Mobile and/or swarm tomography is used in various applications. For example, nuclear detectors are used in conjunction with drones or other vehicle(s) to assess the spatial distribution of nuclear sources. This scanning may be performed in a medical application, but security, geosensing, and radiation protection applications may use the scanning.

One vehicle or possibly a swarm of (e.g., automated) vehicle(s) transports one or more detectors. Depending on the application, a trajectory is flown to acquire sufficient data for tomographic reconstruction. The scanner adapts to the application and the target area or patient in order to run an optimal acquisition e.g. by adapting the formation flown. Autonomous, adaptable scanning is provided. In a medical application, the patient does not have to adapt to the scanner as the scanning device adapts to the environment and the patient. The patient does not have to lie down on a scanner table but may be standing, moving, or resting in a hospital bed. The use of drones, robots or any autonomous mobile devices allows the scanner equipment to move around the object or patient being imaged. The scanner adapts to the object or patient and environment.

Figure 1:
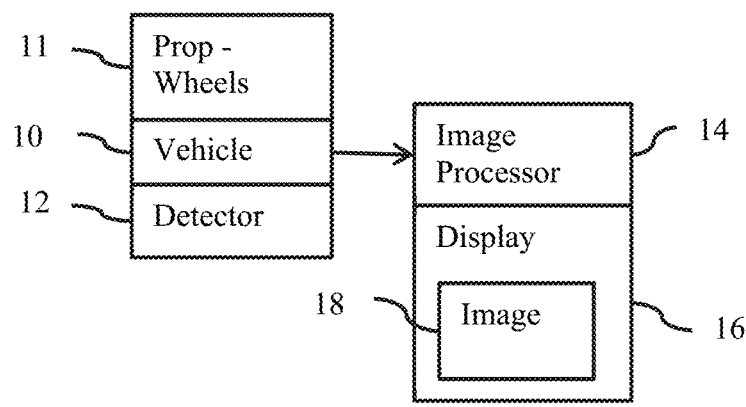
FIG. 1 is tomography imaging system according to one embodiment.
Figure 2:
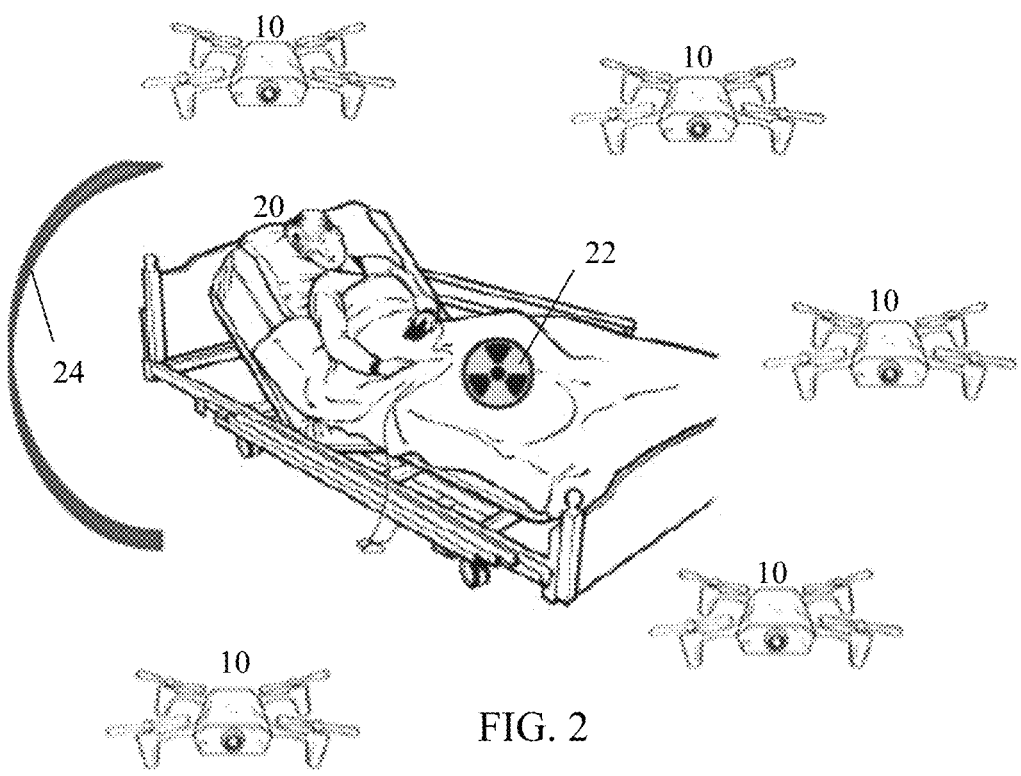
FIG. 2 shows drones for tomography imaging in an example medical application.
Figure 3:
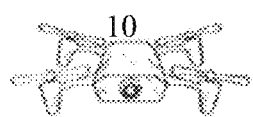
FIG. 3 shows drones for tomography imaging in another example medical application.
Figure 3:
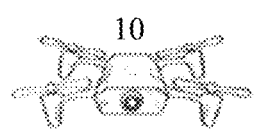
Figure 3:
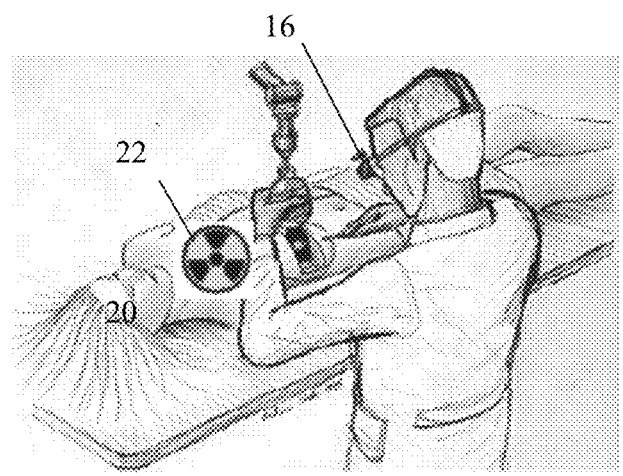
Figure 3:
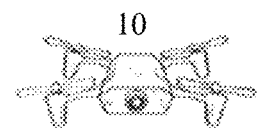
Figure 3:
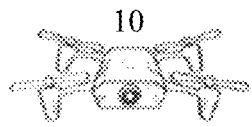

FIG. 1 shows one embodiment of a tomography imaging system. The tomography imaging system is for any of various applications. For example, medical imaging is provided, such as shown in FIGS. 2 and 3. The medical imaging may be SPECT, PET, CT, or other tomography (ultrasound or surgical) imaging system. Diagnostic, theranostic, dosimetry, or surgical support imaging may be provided. As another example, geosensing is provided, such as for sensing the location of objects for mining. In another example, security imaging is provided, such as sensing radiation from a person, luggage, building, ship, or vehicle (see FIGS. 4 and 5). In yet another example, an agriculture tomography imaging application is provided, such as for sensing emissions from foliage. As another example, the tomography imaging system is used for non-destructive material examination.

Any application for imaging the interior of an object and/or imaging radiation may be provided. A tomography medical imaging system is used in the examples below, but the tomography system may be used in other applications.

Figure 6:
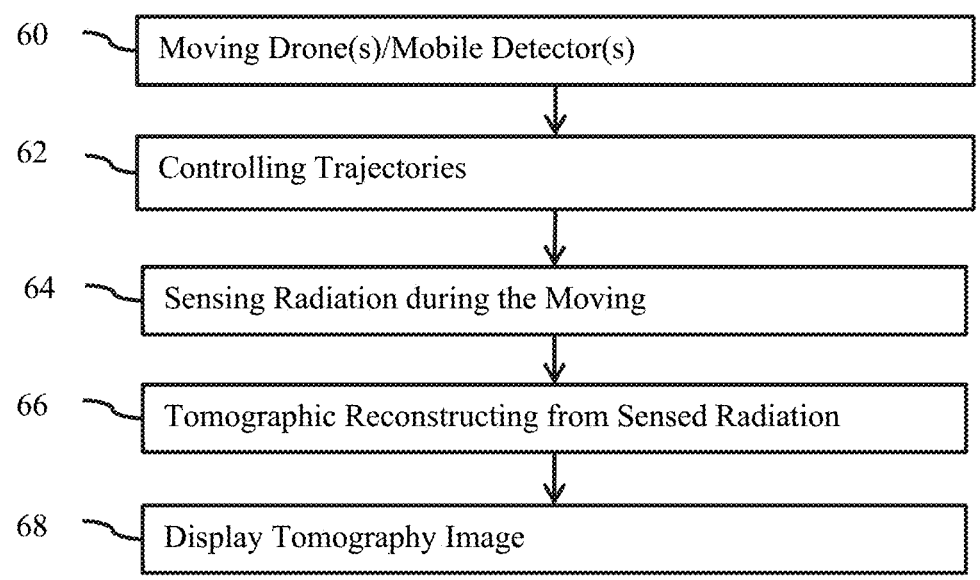
FIG. 6 is a flow chart diagram of one embodiment of a method for tomography imaging using mobile detectors.

The tomography imaging system implements the method of FIG. 6 or another method. A mobile detector is used to move around the object (e.g., patient) being scanned without requiring a gantry and/or positioning of the patient in a bed mounted to the scanner. Radiation from the object is sensed and used in tomographic reconstruction.

The tomography imaging system includes one or more vehicles 10 with detectors 12, an image processor 14, and a display 16. Additional, different, or fewer components may be provided. For example, the display 16 is not provided. While shown as a separate device, the image processor 14 may be on or part of the vehicle 10.

FIG. 1 shows one vehicle 10. Any number of vehicles 10 may be provided, such as the five of FIG. 2, four of FIG. 3, two, three, or more. With one detector 12 for each vehicle 10, a plurality of mobile detectors is provided. 1 to n detectors are held and actively or passively transported by 1 to m vehicles 10 where n and m are integers. N equals m, but may not be equal in other embodiments. A swarm of vehicles 10 may be used, such as three or more.

Each of the vehicles 10 is separate from other vehicles 10. There is no physical connection between the vehicles 10. Each of the vehicles 10 may move independently of the other vehicles 10. Separate housings are provided. An indirect connection through the ground, wall, ceiling, or air may occur, but there is no direct connection or connection through an engineered object (e.g., no cable or mechanical linkage).

In one embodiment, the vehicles 10 are drones. Each drone includes a battery for power, transceiver for communication, engine, props or blades 11 for mobility, and the detector 12. In other embodiments, the vehicles 10 are wheeled, tracked, or legged (walkers) for independent movement. For example, each vehicle 10 includes wheels 11 for mobility, an engine and power source (e.g., battery), transceiver, and the detector 12. Other robots or robotic vehicles 10 may be used. A processor and/or sensor may be included for autonomous navigation. Guided (e.g., remote control) or user-controlled navigation is used in other embodiments.

One or more sensors for position determination may be provided, such as a camera, range sensor, ultrasound sensor, and/or global positioning sensor. The sensor or sensors are on each vehicle 10, and/or a sensor or sensors detect the position of the vehicles 10 remotely.

In an alternative embodiment, the vehicles 10 have connectors or other releasable devices for manual change in position. For example, each vehicle does not include an engine but does include a magnetic or other connector. The vehicle 10 may be repositioned to different locations, such as on walls, floor, or ceiling or other surrounding structure. The separate vehicles 10 are positioned for sampling and then repositioned for further sampling to tomographically image an object.

The vehicles 10 actively or passively move in space, each as a single independent device. Passive movement may be provided using gravity. Each vehicle 10 moves independently, so may move in a different direction than other vehicles 10. The movement may be in two (e.g., across a floor or the ground) or three (e.g., flying in the air) dimensions.

For movement, the vehicles 10 may be operated individually, in pairs, or as a swarm. Any formation may be used, such as independent trajectories with collision avoidance, paired trajectories to follow a same or similar orbit, or swarm-based trajectories with randomized or other trajectories. The vehicles 10 may be self-organizing in a swarm. Alternatively, a processor optimized, predetermined, or other planned trajectory pattern is used for one, more, or all the vehicles 10. In an application where multiple vehicles 10 operate independently, a swarm intelligence and/or an automatic collision avoidance system may be used.

Since the vehicles 10 are not constrained to a single track or fixed connection to the floor, ceiling or wall, the constraint for direct planar imaging and using a detector 12 sized to the object is removed. The detectors 12 may be smaller than the internal region to be imaged since the vehicle 10 may move the detector 10 about the object (e.g., patient). One or more small detectors 12 with location sensing may execute coordinated or controlled acquisition patterns to optimally acquire data from a much larger field of view for tomographic imaging.

The mobility of the vehicles 10, such as being able to move over tens or more of meters, allows the vehicles 10 and corresponding scanning to move to the object rather than bringing the object to the scanner. For example, the vehicles 10 travel from one room to another for scanning different patients. The vehicles 10 may travel from storage to a patient. For example, FIG. 2 shows the vehicles 10 as drones following trajectories 24 to scan a patient 20 for radiation emission 22. The patient 20 is in a hospital bed for the patient 20 (not dedicated to scanning). The drones move to the room with the patient 20 to scan the patient. FIG. 3 shows another example where the drones move to the surgical suite or room, allowing both surgery and scanning in the same room.

Figure 4:
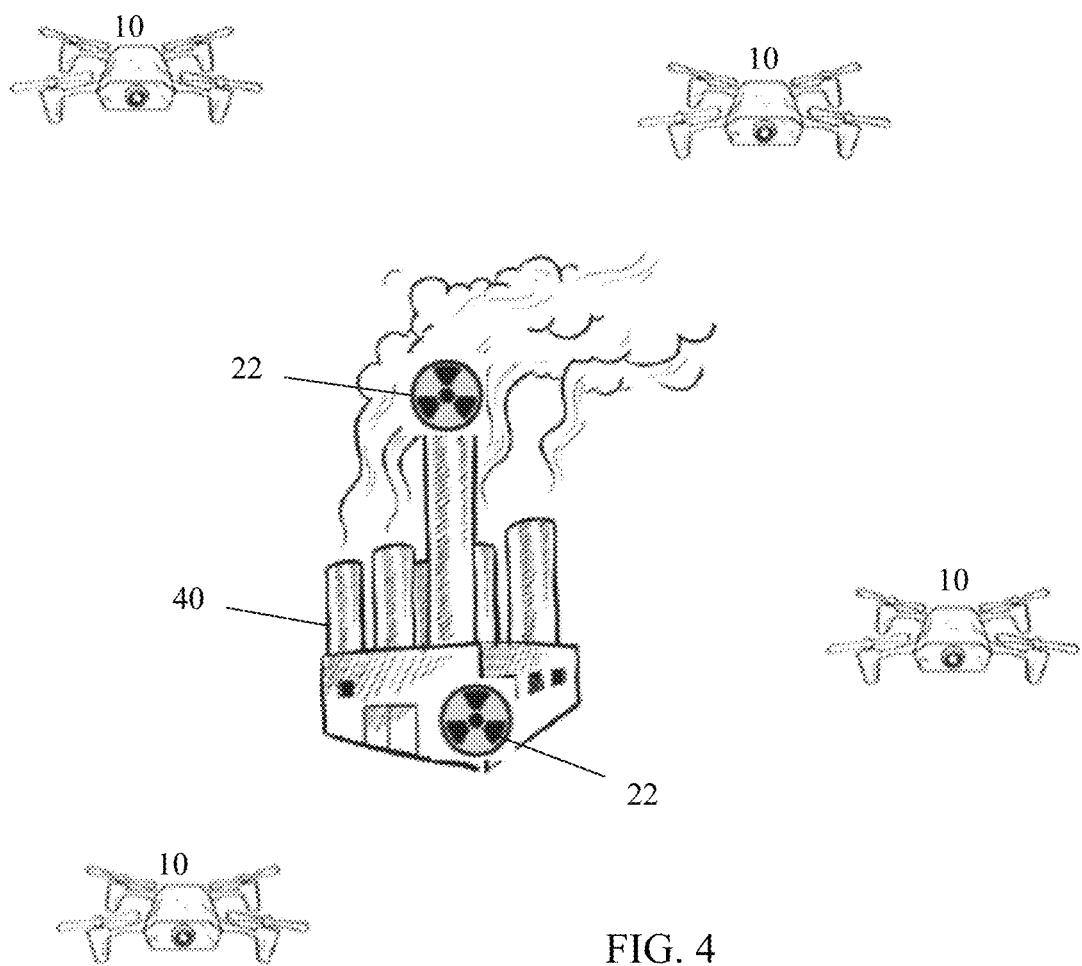
FIG. 4 shows drones for tomography imaging in an example industrial or security application.
Figure 5:
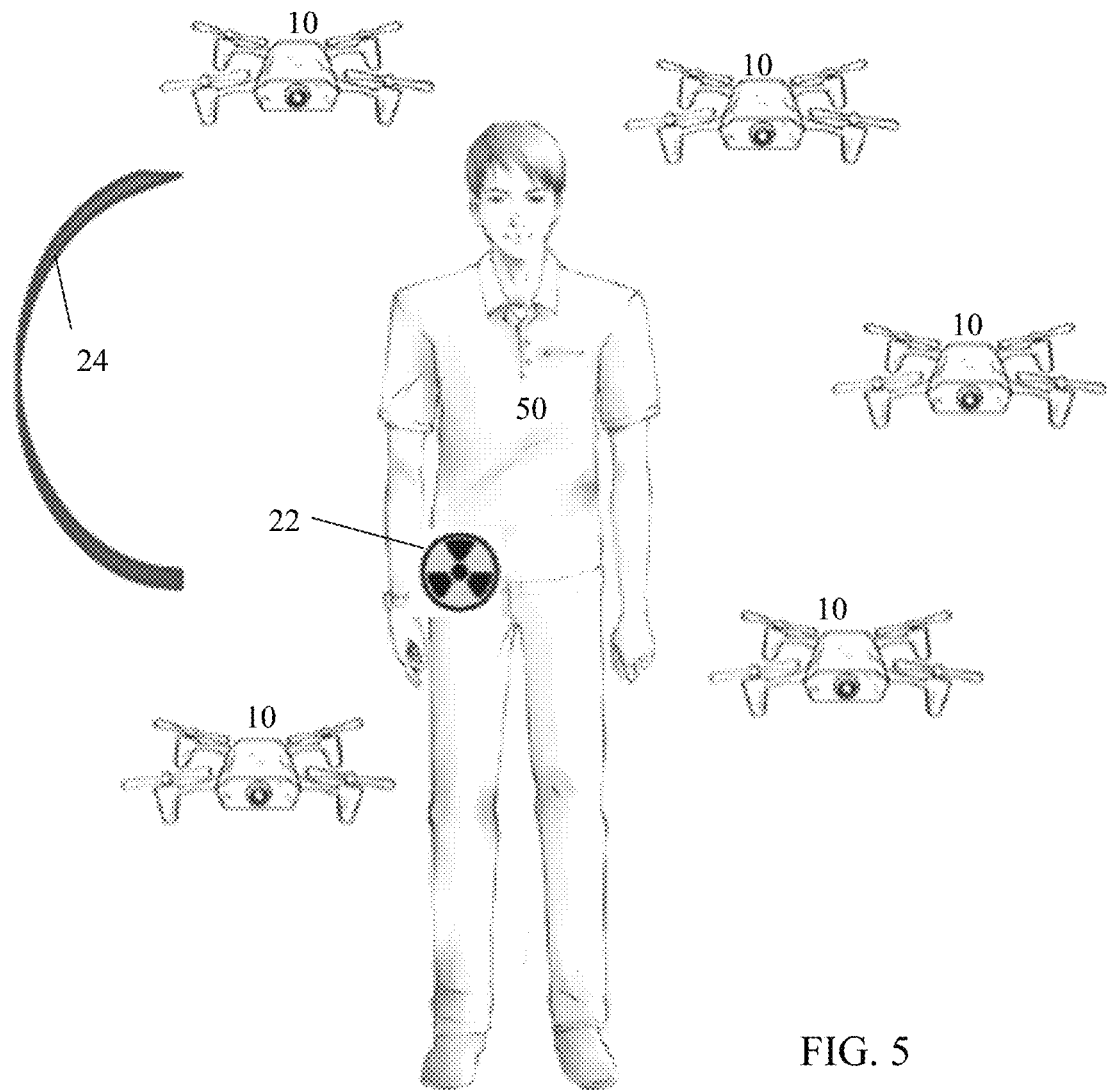
FIG. 5 shows drones for tomography imaging in another example security application.

FIG. 4 shows an example in an industrial or security application. The drones move to the building 40 of interest to scan the building for radiation 22. FIG. 5 shows an example in a security application. The drones move to a person 50 (e.g., a passenger) to scan rather than requiring the person 50 to lay down in or stand in a scanner.

The vehicles 10 may include a position sensor to detect position relative to each other, the local environment, and/or global position. Alternatively, the position of the vehicles 10 is determined by image processing or other capture of the formation of the vehicles about the object.

Each or most of the vehicles 10 includes a detector 12. The detector 12 detects radiation from the patient. For example, emissions from radioactive decay are detected. Gamma radiation is detected. As another example, x-ray radiation passing through the patient is detected.

The detector 12 is of any size based on weight and space limitations of the vehicle 10. In one embodiment, the detector 12 is 10×10 cm, 5×5 cm, 3×5 cm or 5×7 cm, but other sizes may be used. Any shape, such as a flat or curved plate that is square, rectangular, or another shape, may be used.

The detector 12 is a solid-state detector, such as being a semiconductor. For example, a CZT or other direct conversion gamma ray detector is used. Other solid-state detector modules include Si, CZT, CdTe, HPGe or similar devices. The detector 12 is created with wafer fabrication at any thickness, such as about 4 mm for CZT. Alternatively, the detector 12 is another type of sensor, such as a crystal layer and photomultiplier tubes.

The vehicle 10 and/or detector 12 may include a semiconductor formatted for processing. For example, the detector 12 includes an application specific integrated circuit (ASIC) for sensing photon interaction with an electron in the detector 12. The ASIC is collocated with the pixels of the detector 12. The ASIC is of any thickness. A plurality of ASICs may be provided, such as 9 ASICS in a 3×3 grid of the detector 12.

The detector 12 may operate at any count rate. Electricity is generated by a pixel due to the interaction with radiation. This electricity is sensed by the ASIC. The location, time, and/or energy is sensed. The sensed signal may be conditioned, such as amplified, and sent to a transceiver for wireless communication.

A collimator may be included in or by the detector 12. Alternatively, no collimator is provided.

For PET, SPECT, or other nuclear scanning, the detectors 12 detect emissions from the radioactive decay. For x-ray radiation, the detectors 12 detect energy from transmission to or through the patient. The trajectory 24 of one vehicle 10 is matched with a trajectory 24 of another vehicle 10. One vehicle 10 includes the detector 12, and the vehicle opposite the patient 20 includes a transmitter, such as an x-ray source. For transmission tomography applications, two or more vehicles 10 move and operate in unison to be able to form a transmission image of the object, material, or human being imaged.

The wireless communications are used to synchronize the clocks of the vehicles 10. One vehicle 10 or a base station provides a master clock to which the clocks of the other vehicles 10 synchronize. For example, the image processor 14 has a master clock. Wireless communications are used to synchronize the clocks of the vehicles 10 with the master clock and/or to determine temporal offset of the clocks of the vehicles from the master clock. The synchronization allows for PET imaging to operate on paired events detected by different detectors 12. Unsynchronized clocks may be used in other embodiments.

The wireless communications are used to transmit detected signals (e.g., emission or decay events). Each vehicle 10 transmits the detected signals, such as the time, energy, and location of detection. The transmissions are direct to a master device, such as the image processor 14 (e.g., computer, tablet, or workstation hosting the image processor 14), or are transmitted to another vehicle 10. Mesh or other distributed network communications may be used.

The image processor 14 is a general processor, digital signal processor, application specific integrated circuit (ASIC), field programmable gate array, graphics processing unit, digital circuit, analog circuit, and/or another now known or later developed processor for performing tomography. The image processor 14 may be formed from multiple devices, such as an ASIC for pairing events and determining angle of coincidence (e.g., PET), a general processor for tomographic reconstruction, and a graphics processing unit for rendering an image from the tomographically generated representation of the interior of the object. Parallel and/or serial processing may be used. The image processor 14 is configured by hardware, firmware, and/or software.

The image processor 14 is configured to generate a tomographic image, such as a SPECT, PET, or CT image. The counts and the positions on and of the detectors 12 (i.e., positions indicating the lines of response) are used to reconstruct a two or three-dimensional representation of the patient. The image processor 14 determines the lines of response for the measurements (e.g., x-ray intensity or emission occurrence with or without energy). The image processor 14 is configured to identify lines of response for the signals.

The image processor 14 is configured to tomographically reconstruct a two or three-dimensional representation from the lines of response. Any tomographic reconstruction may be used. In an iterative process, such as using forward and backward projection from measurement space to object or image space, a spatial representation of the object is generated by optimization. The scanner (e.g., vehicles 10) is represented as a system model used in the reconstruction. The image processor 14 determines a spatial distribution based on the signals and the system model. The spatial distribution is a two or three-dimensional distribution. A two or three-dimensional representation of an internal region of a patient or another object is generated by tomography from signals of the detectors 12. The locations of emissions are represented for PET or SPECT, and the locations of density or x-ray attenuation are represented for CT.

The image processor 14 is configured to generate an image 18 from the representation. Volume, surface, or other rendering may be performed for a three-dimensional representation. The three-dimensional distribution is rendered to a two-dimensional image 18 for display from a given viewing direction. Alternatively, a slice or plane represented in the three-dimensional representation is used to select data to form a two-dimensional image 18. For a two-dimensional distribution or representation, a two-dimensional image 18 is generated.

The image processor 14 is configured to control the trajectory 24 for one or more (e.g., each) of the vehicles 10. The control is a direct mapping or setting of the trajectories, indirect setting of a value of a variable used in forming the trajectories, and/or indication of desired sampling locations or time used by the vehicles 10 to form the trajectories. For tomography, Orloff's sphere sampling may be used to satisfy the Tuey condition. The trajectories 24 are controlled to provide sufficient sampling for reconstruction of the representation. The trajectories 24 are based on the sampling pattern (e.g., even distribution over all or part of a sphere or surrounding shape conceptually formed around the object being scanned) for the tomographic reconstruction.

Since reconstruction is iterative, the image processor 24 may control the trajectories 24 differently at different times. For example, a reconstruction may result from under sampling at one or more locations and/or orientations. The trajectories 24 may be controlled to then acquire more data or samples for the locations and/or orientations associated with under sampling. At least part of the trajectory 24 is based on the previous reconstruction (i.e., iteration in the optimization). In one embodiment, a live feed of data (signals) is sent to an acquisition system, and an image of a reconstructed object is displayed and possibly reviewed by a person. An operator, who can oversee and possibly drive the trajectories 24 of the vehicles 10 and/or define regions of interest, causes the image processor 14 to alter or use the trajectories 24 to correct any undersampling and/or to increase resolution. In other embodiments, the image processor 14 controls to correct undersampling or increase resolution without user input. An "on-the-fly" reconstruction helps to adapt and drive the trajectories 24 being followed by the vehicles 10.

The trajectories 24 are orbits, lines, curves, or other motion over time about or near the object. The trajectories 24 may include dwell time, such as holding position at a location and/or orientation (e.g., no motion as part of the trajectory 24). The trajectory 24 may include one or more locations with dwell time and may include paths to move between the locations. Alternatively, the trajectory 24 is formed entirely of non-zero motion or of discrete locations.

The trajectory 24 may be pre-planned. Alternatively, the trajectory 24 is created or planned based on the object size, position, orientation, and/or motion. The values of one or more variables for the object and/or environment are used with the desired sampling for tomography to calculate the trajectories. In one embodiment, the vehicles 10 are self-organizing. Randomization or other approach may be used to create trajectories 24, such as using a robot swarm approach. The image processor 24 may then guide or cause alteration of one or more trajectories 24 to sample from one or more needed or under-sampled locations for the tomography. The randomization may be pseudo random, allowing for constraints or increased probability for desired sampling locations to be included in the trajectories 24.

The trajectories 24 account for the object position, object movement, and/or environment. The ground or other obstructions (e.g., bed, walls, posts, other people, or furniture) are accounted for in the trajectories 24. For example, the trajectories 24 of the vehicles 10 in FIG. 2 are planned to move about the patient 20 without contacting the floor, bed, or patient 20. The trajectories 24 are planned to have a given distance or within a range of distances away from the patient 20, to be on a conceptual sphere fit to the patient 20 and accounting for obstructions, and/or change curvature at different portions to account for the orientation of the patient 20. In another example, the patient 20 is walking. The trajectories 24 account for the change in patient position in order to sample for tomography by re-centering an orbit or changing curvature or position based on patient change in position.

The trajectories 24 of the vehicles 10 are planned or incorporate collision avoidance to avoid obstructions and/or each other. The trajectories 24 may incorporate constraints of the vehicles 10, such as being speed limited and/or constrained to be on the ground for wheeled vehicles 10.

The scanner formed by the detectors 12 on the vehicles 10 uses the mobility of the vehicles 10. The scanner adapts to the object (e.g., patient) and the environment. Rather than a fixed-in-place scanner requiring the patient to adapt to the scanner, the scanner uses the mobility of the vehicles 10 to adapt to the object.

The display 16 is a CRT, LCD, projector, printer, or other display. The display 16 is configured to display the tomographic image 18. The image 18 or images 18 are stored in a display plane buffer and read out to the display 16. The images 18 may be a sequence of images generated for different iterations in the reconstruction as the sampling is updated. A final image 18 may be displayed without display of images prior to completion of the scan. The image 18 or images 18 are of the two or three-dimensional representation of the internal region of the object, so represent a view of the interior of the object. Images representing an exterior view may be generated, such as a view of an agricultural field.

In one embodiment, the image 18 is an augmented reality image. The display 16 is an augmented reality display by showing an image of the patient augmented with reconstructed data (e.g., an optical image of the patient with a color, greyscale, or symbol (marker) overlay based on the tomographically reconstructed representation). FIG. 3 shows an example where glasses, virtual reality googles, or other augmented display 16 is worn by the user. Rather than an optical image, the actual view of the patient 20 by the physician is augmented with a projection or image from the scanning. Real time feed of images 18 and reconstructed data to a virtual, mixed, and/or augmented reality displaying device is provided for the operator (physician, technician) for real time evaluation. Raw and reconstructed data is used for imaging on a monitor display, or an augmented, mixed or virtual reality device is used.

FIG. 6 shows one embodiment of a flow chart of a method for tomography imaging, such as medical tomography imaging. Mobile or movable, separate detectors are used to scan. By controlling the trajectories (e.g., placement) of the mobile detectors, data for tomographic reconstruction is acquired based on the object and the environment.

The method may be implemented by the system of FIG. 1, the drones of FIGS. 2-5, or other arrangements. Vehicles with detectors or moveable detectors are positioned according to trajectories (e.g., placement at different sampling positions) and sense signals from the object. An image processor or another processor controls the trajectories for sampling used in the tomography. The image processor reconstructs a representation of the interior of the object from the signals by tomography. A display screen displays the resulting tomographic image. Other systems or devices may be used.

The acts are performed in the order shown (i.e., top to bottom or numerically) or other orders. For example, acts 60, 62, and 64 are performed simultaneously or repetitively. As another example, act 66 may be performed while act 64 is being performed.

Additional, different, or fewer acts may be provided. For example, act 62 is not performed as an active control, but instead the mobile detectors move independently and sample until a controller determines that sufficient information is obtained. As another example, act 68 is not performed, such as where the image or reconstructed representation is saved to a memory or transferred over a computer network. In yet another example, acts for user input and control are provided, such as user change to the trajectories used in act 60.

In act 60, a drone or other mobile vehicle with a detector moves or is moved. The movement uses the mobility of the drone or vehicle to move about the object, such as to orbit a patient, drive around the object, walk around the object, or be placed around the object. The movement is along a trajectory, such as a sequence of locations for sampling for tomography or a path through locations for sampling. The trajectory is used for sampling radiation from different positions relative to the object.

Other drones or mobile vehicles with detectors may move relative to the object being scanned and/or each other. One or more separate detectors are moved around or near the object to sense radiation from different locations and/or angles relative to the object. In one embodiment, multiple drones or other mobile vehicles self-organize as a swarm. The movement is based on the swarm approach being used, such as randomized movement constrained in space, speed, and/or collision avoidance, or a formation (e.g., the number of detectors and/or the spatial relationship of the detectors to each other).

The movement accounts for the environment and the object being scanned. Obstructions may be avoided. The trajectories may be set to position within a desired range from different locations about the object. The position and/or orientation of the object results in different trajectories to provide the desired sampling. Where the object is moving, such as a walking person or a person waving their arms, the trajectories may be set or altered to account for the motion. For example, the drones move based on movement by the patient and the desired sampling. The movement avoids collision with the moving object and samples from the desired range as the object moves.

In one embodiment, the mobility of the detectors is used for convenience. The detectors move from one location to a different location (e.g., a different room) to scan the object. For example, drones fly from a storage room or location of a previous scan to another location (e.g., a hospital room) for scanning a patient at the other location.

In act 62, a person or processor controls the trajectories based on the sampling for tomographic reconstruction. The control is by pre-planning, active control during movement or placement, and/or control by feedback. The mobile detectors (e.g., drones) are controlled or self-control to sample from the locations and/or at angles to provide for tomographic reconstruction. The dwell time at each location and/or angle, speed of movement, path along which to move, and/or other characteristic of the placement of the detector for sampling in tomography imaging is controlled.

The control may be a change in trajectory. The trajectory is altered to further sample from a location and/or angle relative to the object, such as where a reconstruction using tomography shows under sampling. The change may be due to an obstacle, change in position of an obstacle, and/or movement of the object (e.g., patient). The trajectory of movement is changed to account for the object and environment while providing the desired sampling for tomography.

In act 64, the detector on the drone or other mobile vehicle senses radiation from the object (e.g., the patient). A solid state or other detector detects x-rays, gamma rays, photons, or other radiation from the object. For example, the patient ingests a radiopharmaceutical or an object may include a radioactive source. Emissions from decay are detected. As another example, a transmitter transmits the radiation (e.g., x-ray radiation) through the object, and the radiation as altered by the object is detected.

The sensing occurs during the moving of act 60. The movement of act 60 may include stationary positions during which sensing occurs. Alternatively, the sensing occurs while or as the detector moves with a non-zero speed. The movement may include translation and/or rotation.

For PET, different photons or gamma rays from a same emission may be detected along a line of response. Timing and energy may be used to match the detections as an event. For SPECT, a count of emissions along a given angle at a given position is performed. For CT, the topogram or projection in two-dimensions showing the attenuation of x-rays through the patient is detected.

The detected events from different sampling locations are counted or collected. The lines of response or lines along which the different events occur are used in reconstruction. The lines of response are based on the position and/or angle of the detector when the event occurred. The distribution in three dimensions of the emissions from or x-ray attenuation of the object may be reconstructed from the events and corresponding lines of response.

In act 66, an image processor tomographically reconstructs an image of an internal region of the patient from the sensed radiation of act 64. The lines of response and events are used to reconstruct a two or three-dimensional representation of the object. CT, PET, SPECT, or other reconstruction is used. In an iterative optimization, the locations of emissions or the attenuation at the locations is determined from the detected signals. For PET or SPECT, tomographic reconstruction is used to reconstruct the locations of the radioisotope. For CT, tomographic reconstruction is used to reconstruct the attenuation at locations throughout the object.

A spatial distribution representing an exterior of the object or objects may be reconstructed. For example, the locations of emissions in an agricultural field is reconstructed. The object being represented is emissions from or transmissions through a patient, building, underground mineral deposit, person, luggage, vehicle (e.g., truck, plane, or boat), or other object.

In act 68, a display displays an image. The image processor generates an image from the reconstructed representation. An image for two-dimensional display is formed or rendered from the representation. The image may be formed by interpolation, display value (e.g., color) mapping, filtering, and/or other image processing.

The displayed image is a view of an internal plane or volume of the object. The detected emissions or densities of the object are displayed. For example, a PET, SPECT, or CT image is generated as a three-to-two-dimensional rendering or as a planar image. For gamma ray radiation, the image may represent a spatial distribution of emissions. The result may be a map of uptake in a patient or location in another object of radiation emission. This internal (or external) view of the object may assist in localizing structure of interest, such as function in a patient, a radioactive source, a flaw in a material, or other structure.

The image is displayed on a display screen. Alternatively, the image is printed or projected. The image may be combined with a view or other image in an augmented reality display, a virtual display, or a mixed display.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A tomography medical imaging system comprising:
    a plurality of separate vehicles, each of the separate vehicles independently movable in two or more dimensions, each of the separate vehicles having a detector;
    an image processor configured to generate a two or three-dimensional representation of an internal region of a patient by tomography from signals of the detectors; and
    a display configured to display an image of the two or three-dimensional representation of the internal region of the patient.

2. The tomography medical imaging system of claim 1 wherein the plurality comprises three or more of the separate vehicles.

3. The tomography medical imaging system of claim 1 wherein the separate vehicles comprise drones moveable in three dimensions.

4. The tomography medical imaging system of claim 1 wherein the separate vehicles comprise wheeled, tracked, or walking vehicles.

5. The tomography medical imaging system of claim 1 wherein the image processor is configured to control a trajectory of each of the separate vehicles, the trajectories based on a sampling pattern for the tomography.

6. The tomography medical imaging system of claim 1 wherein the detectors comprise solid state gamma ray detector.

7. The tomography medical imaging system of claim 1 wherein the separate vehicles are self-organizing.

8. The tomography medical imaging system of claim 1 wherein the separate vehicles are configured to travel to the patient from one room to another room.

9. The tomography medical imaging system of claim 1 wherein the display comprises an augmented reality display.

10. The tomography medical imaging system of claim 1 wherein the image processor is configured to reconstruct by the tomography iteratively, and control the trajectories of the separate vehicles based, at least in part, on a previous reconstruction by the tomography.

11. The tomography medical imaging system of claim 1 further comprising a transmitter on one of the separate vehicles of the plurality or on another vehicle, and wherein the detectors are configured to detect energy responsive to a transmission from the transmitter.

12. A method for medical tomography imaging, the method comprising:
    moving a drone with a detector, the drone moving about a patient;
    sensing radiation from a patient with the detector during the moving;
    tomographically reconstructing an image of an internal region of the patient from the sensed radiation; and
    displaying the image.

13. The method of claim 12 wherein moving comprises moving the drone along a trajectory and sensing comprises sampling the radiation from different positions of the trajectory, and further comprising controlling the trajectory based on the sampling for the tomographically reconstructing.

14. The method of claim 12 wherein sensing comprises sensing with a solid-state nuclear detector.

15. The method of claim 12 further comprising moving other drones with other detectors, the drone and other drones comprising a self-organizing swarm.

16. The method of claim 12 wherein moving comprises moving based, at least in part, on movement by the patient.

17. The method of claim 12 wherein moving comprises the drone flying from a first location to a second location, the patient being at the second location.

18. A tomography imaging system comprising:
    a swarm of mobile detectors, each of the mobile detectors independently movable in two or more dimensions;
    an image processor configured to generate, by tomography from signals from the mobile detectors, a two or three-dimensional representation of an internal region of an object; and
    a display configured to display an image of the object from the two or three-dimensional representation of the internal region.

19. The tomography imaging system of claim 18 wherein the object is a patient, and wherein the mobile detectors comprise drones with gamma ray detectors.

20. The tomography imaging system of claim 18 wherein the mobile detectors of the swarm are configured to follow trajectories based, at least in part, on sampling for the tomography.

* * * * *